(12) United States Patent
Degian

(10) Patent No.: US 9,125,795 B2
(45) Date of Patent: Sep. 8, 2015

(54) BLOOD SUGAR MANAGEMENT SYSTEM

(71) Applicant: Tania Degian, Toronto (CA)

(72) Inventor: Tania Degian, Toronto (CA)

( * ) Notice: Subject to any disclaimer, the term of this patent is extended or adjusted under 35 U.S.C. 154(b) by 205 days.

(21) Appl. No.: 13/937,370

(22) Filed: Jul. 9, 2013

(65) Prior Publication Data

US 2013/0292409 A1 Nov. 7, 2013

Related U.S. Application Data

(63) Continuation-in-part of application No. 13/088,567, filed on Apr. 18, 2011, now abandoned.

(60) Provisional application No. 61/361,547, filed on Jul. 6, 2010.

(51) Int. Cl.
| | | |
|---|---|---|
| B65D 83/08 | (2006.01) | |
| A61J 1/00 | (2006.01) | |
| A61M 15/00 | (2006.01) | |
| A61K 31/7004 | (2006.01) | |
| A61K 31/7016 | (2006.01) | |

(52) U.S. Cl.
CPC .............. *A61J 1/00* (2013.01); *A61K 31/7004* (2013.01); *A61K 31/7016* (2013.01); *A61M 15/0051* (2014.02); *B65D 83/0829* (2013.01); *G01N 2800/042* (2013.01)

(58) Field of Classification Search
CPC ............ B65H 37/005; A61M 15/0051; B65D 83/0829; B65D 83/0823
USPC ....................... 221/7, 8, 22, 25, 26, 32, 70, 73
See application file for complete search history.

(56) References Cited

U.S. PATENT DOCUMENTS

| | | | | |
|---|---|---|---|---|
| 4,832,229 | A * | 5/1989 | Hackmann et al. | 221/25 |
| 8,113,199 | B2 * | 2/2012 | Augustyn et al. | 221/7 |
| 8,322,262 | B2 * | 12/2012 | Ryu | 221/30 |
| 8,499,965 | B2 * | 8/2013 | Sheffield | 221/45 |
| 8,672,181 | B2 * | 3/2014 | Schneider | 221/272 |
| 2005/0089548 | A1 * | 4/2005 | Virgalitto et al. | 424/440 |
| 2005/0092763 | A1 | 5/2005 | Haggerty | |
| 2007/0170196 | A1 | 7/2007 | Libobova | |
| 2009/0200330 | A1 * | 8/2009 | Giraud | 221/46 |
| 2013/0052234 | A1 | 2/2013 | Goldberg | |

* cited by examiner

*Primary Examiner* — Timothy Waggoner
(74) *Attorney, Agent, or Firm* — Daniel Boudwin; Global Intellectual Property Agency LLC

(57) ABSTRACT

The present invention is a system for managing blood sugar levels while on the go. A roll of water soluble sugar thin-film is contained within a specialized dispensing container. A sliding button is disposed on one side of the dispenser and actuates dispensing of a single sugar strip and advancement of a counter. Each sugar strip contains a predetermined dose of dextrose or other sugar in a rapidly dissolving oral film. Thus, diabetics and persons experiencing a blood sugar imbalance can rapidly dispense a measured dose of sugar that dissolves in saliva. A counter on the side of the dispenser tracks the number of remaining sugar strips, thereby ensuring that users who rely on ready availability of sugar strips are aware of their remaining supply.

8 Claims, 5 Drawing Sheets

BLOOD SUGAR MANAGEMENT SYSTEM

CROSS REFERENCE TO RELATED APPLICATION

This application claims the benefit of U.S. Provisional Application No. 61/361,547 filed on Jul. 6, 2010 entitled "Sugaraid." This application is a continuation in part of U.S. Non-Provisional Utility patent application Ser. No. 13/088,567, filed on Apr. 18, 2.011 and entitled "Rapidly Dissolving Oral Strip of Sugar for Hypoglycemia." The patent applications listed herein are incorporated here by reference in its entirety to provide continuity of disclosure.

BACKGROUND OF THE INVENTION

Field of the Invention

The present invention relates to a system and method for managing blood sugar levels. The system includes a dispenser unit that houses a roll of rapidly dissolving sugar strips. A counter on the dispenser provides an indication of the number of strips remaining in the roll. Each sugar strip contains a premeasured dose of sugar so that users can determine how many strips they need to ingest based on their personal blood sugar level. The invention will be appreciated by those with diabetes, eating disorders, and other conditions that cause blood sugar fluctuations requiring regular sugar intake.

Low blood sugar concentration (hypoglycemia) is a common problem experienced with people who suffer from diabetes, as well as those with eating disorders. Common symptoms of low blood sugar episodes include mental confusion, dulled cognitive ability, fatigue, shaky or unstable limbs, and hunger. As blood sugar levels continue to drop these symptoms become more pronounced and severe. In some cases prolonged low blood sugar concentration can lead to fainting, coma, or even death.

Low blood sugar concentration episodes occur as a result of imbalance in a person's insulin production, food intake, and exercise habits. In persons with diabetes, insulin production is low, additional insulin is taken via pills or injections. The uncertainty of natural insulin production sometimes results in spontaneous abundances and shortages, thereby creating swings in sugar processing and blood sugar levels. Similarly, persons suffering from eating disorders do not intake food at regular intervals, sometimes purging eaten food through vomiting. Because overall food intake is low, the body's natural insulin production rapidly processes sugar, leaving blood sugar levels low.

A person's ability to sense the decline of blood sugar concentration is generally linked to the regularity of their average blood sugar levels. Persons with relatively minor fluctuations in their average blood sugar will find it easier to identify the signs and symptoms of a low blood sugar episode. Conversely, those who experience frequent spikes and drops in blood sugar levels will find it difficult to identify the onset of a hypoglycemic episode. This is because the brain adapts to the frequent changes, using them as a baseline for establishing normal body chemistry activity, rather than normalizing body chemistry based on small changes in blood sugar levels. Thus, people with diabetes may not always be aware that their blood concentration is dropping dangerously low.

When hypoglycemic episodes occur the afflicted person must intake sugar before fainting occurs. Juice, food, and candy are commonly ingested by those suffering from low blood sugar episodes to increase blood sugar levels. But these approaches may perpetuate the problem, because the amount of sugar contained in the juice or food may be more than is needed to balance blood sugar levels, resulting in high blood sugar levels (hyperglycemia). Additionally, these items must be digested before blood sugar levels begin to increase.

Sugar packets are a useful alternative to juice and food items, for managing low blood sugar episodes. The sugar granules dissolve in saliva and are absorbed into the blood stream during the process of chewing and swallowing. Because sugar packets contained an approximately measured weight of sugar, they can be more effective that juice or food in controlling blood sugar. But the packets are often messy because the many small sugar granules scatter easily.

An alternative to sugar packets and food is sugar tablets. These tablets are dry pills formed of compressed sugar and a bonding agent. The tablets do not dissolve quickly and must be held under the tongue or swallowed to achieve disintegration. If swallowed, the pills pose a choking hazard because the dry, chalky composition of the pills makes it easy for them to get stuck in the throat passageways.

The current approaches to blood sugar concentration management do not address the need for a consistent, measured sugar dose that is discrete and easy to take at any time. The present invention provides a system that includes a number of water soluble sugar strips, each containing a premeasured amount of sugar, and a dispenser that tracks the number of strips left, to ensure that people needing sugar always have an easy to use and dependable source of sugar.

DESCRIPTION OF THE PRIOR ART

The present invention is a system for managing blood sugar concentration. A dispensing container is included that houses a roll of oral thin film sugar strips. The dispensing container is water resistant, having a flap that covers the strip exit slot, to prevent water from seeping into the dispenser where it can melt the sugar strips. An actuator button disposed on the side of the dispenser lowers the flap and advances the roll of sugar strips until a single strip protrudes through the exit slot. To keep track of the number of sugar strips left in the roll, a counter is included that prominently displays current sugar strip count. The prior art does not teach the elements of the present blood sugar management system. The following list of devices and systems is considered to be a listing of prior art relevant to the present disclosure.

Giraud, US 2009/0200330 A1 teaches a moisture tight dispenser for oral strips. The dispenser holds a roll of oral strips within its interior. A slide button on the side of the dispenser advances the roll, sliding a single strip out through a slot on one end of the dispenser. The dispensing device has a lid that must be opened in order for a user to access the sliding button. The lid keeps moisture out of the dispenser interior but makes it difficult for users to access the oral strips discretely.

Goldberg, US 2013/0052234 A1 discloses edible rapidly dissolving strips having stimulating or depressant agents integrated into the strip. Though it does teach the use of a dispenser for holding a number of the strips, it does not discuss the structure of the dispenser. Based on the context of the disclosure, the word dispenser refers to packaging or a container.

Haggerty, US 2005/0092763 A1 teaches a packaging and dispenser for orally dissolvable strips. The dispenser is a tray and cover that slide together. A slit in the tray feeds oral strips up from the tray so that a user can pick them up. There is no button or advancing mechanism, instead friction is used to push individual strips upward for dispensing.

Libobova, US 2007/0170196 A1 is another oral strip dispenser with a protective lid. The lid is hingeably attached to the top of the container. When the lid is opened an oral strip advances and protrudes upward from the top of the container. Each strip is contained in a water tight pouch having an upper and lower layer. The user removes the pouch containing the strip from the dispenser then removes the strip from the pouch.

These prior art devices have several known drawbacks. These devices do not teach a dispenser and sugar strip combination that is capable of tracking sugar strip usage. Nor does the prior art disclose a button actuated dispenser that provides sugar strips to a user without requiring the user to touch the strips with his or her fingers. It substantially diverges in design elements from the prior art and consequently it is clear that there is a need in the art for an improvement to existing oral thin film dispensing systems. In this regard the instant invention substantially fulfills these needs.

SUMMARY OF THE INVENTION

In view of the foregoing disadvantages inherent in the known types of oral film dispensing systems now present in the prior art, the present invention provides a new blood sugar management system wherein the same can be utilized for providing convenience for the user when rapid sugar intake is needed while on the go.

The present invention is an oral thin film dispensing system that provides unique features useful in the management and control of blood sugar concentration. The system includes a portable, hand-held dispenser designed to fit in the palm of a user's hand. This dispenser contains a roll of sugar strips, each strip having premeasured sugar content. Dosage measurement is important for ensuring that users are able to properly determine the number of sugar strips needed to address their blood sugar deficiencies.

Because users may be in the midst of public situations, meetings, lectures, and the like when sugar strips are needed, keeping the design and use of the device discrete and concealable is a goal of the invention. The size and shape of the dispenser may vary to accommodate aesthetic tastes, but all versions of the dispenser should have a low profile and be easily concealable so as to be discrete when in use. Thus the dispenser may have an exterior housing that resembles a make-up compact, a gentleman's business card holder, or other common items carried by consumers.

The dispenser has an actuator button disposed on one side of the dispenser housing. Depressing and sliding the button along its track lowers the protective flap abutting the exit slot and advances the roll of sugar strips contained within the dispenser. In this way a sugar strip is presented to the user, ready for placement on the tongue or lips, without requiring the use of the hands. The invention thus reduces the exposure of the sugar strips to germs and contaminants. Similarly, the protective flap snuggly abuts the exit flap, keeping water and contaminants out of the dispenser interior volume when the dispenser is not in use.

A counter is provided to assist users with tracking their sugar strip supply. Each dispensation of a sugar strip advances the counter, reducing the count of remaining sugar strips by a single iteration. With this feature, the diabetes management system helps users ensure that they always have an adequate sugar supply on hand, by providing a visual indicator of remaining sugar strip supply, It is therefore an object of the present invention to provide a new and improved blood sugar management system that has all of the advantages of the prior art and none of the disadvantages.

It is therefore an object of the present invention to provide a system that helps people with blood sugar problems ensure that measured doses of sugar are always available.

Another object of the present invention is to provide a discrete and easy to use portable sugar supply.

Yet another object of the present invention is to provide a waterproof and portable dispenser for sugar strips.

Still another object of the present invention is to provide a counter that visually informs users of their remaining sugar supply.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
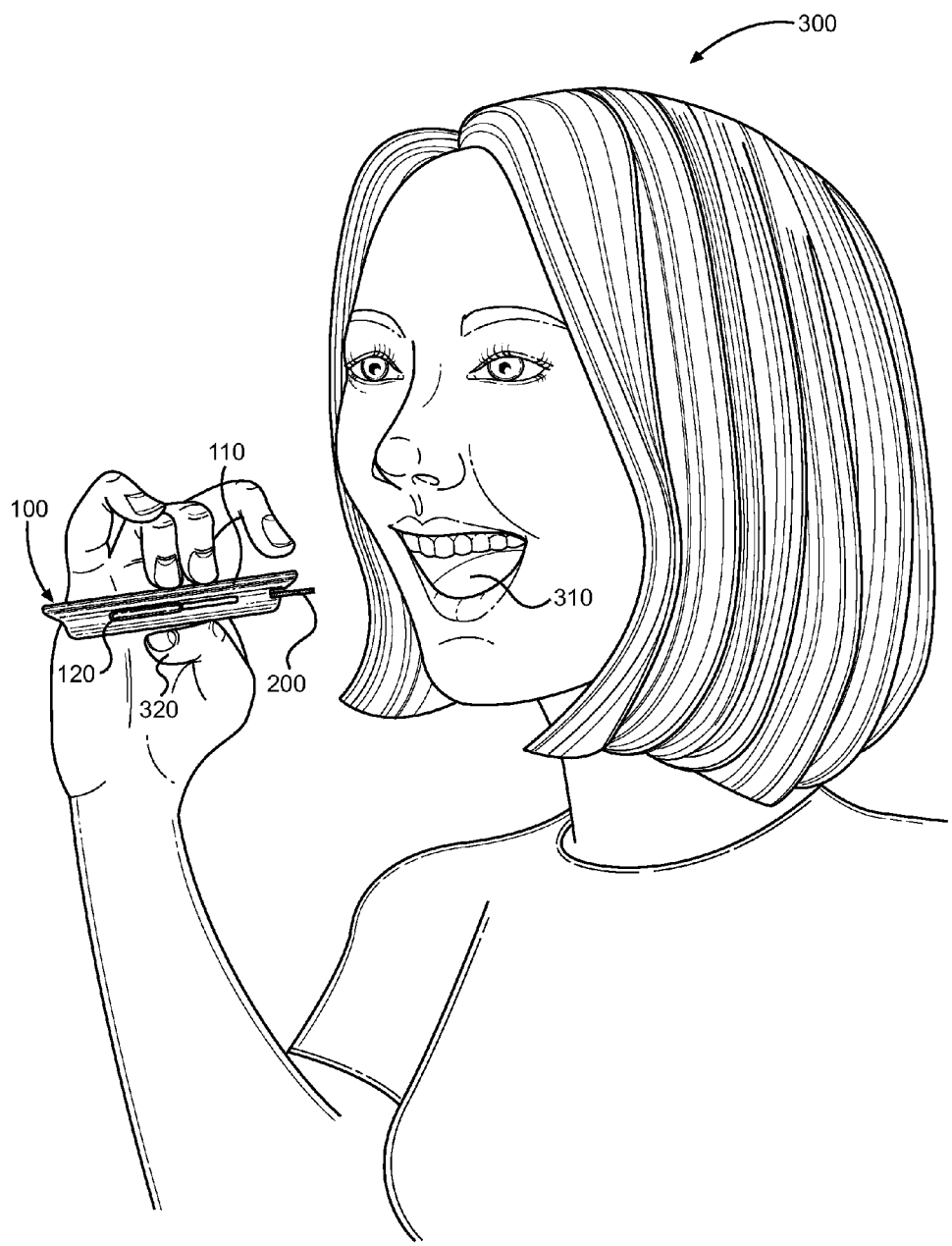
FIG. 1 shows a perspective view of the present system in use. A woman is holding the dispenser, with a sugar strip dispensed and ready for insertion into the oral cavity.

Reference is made herein to the attached drawings. Like reference numerals are used throughout the drawings to depict like or similar elements of the blood sugar management system. For the purposes of presenting a brief and clear description of the present invention, the preferred embodiment will be discussed as used for controlling low blood sugar episodes through the regulated intake of orally dissolvable sugar strips. The figures are intended for representative purposes only and should not be considered to be limiting in any respect.

Referring now to FIG. 1, there is shown a woman using the blood sugar management system. The woman 300 holds the sugar strip dispenser 100 casing 110, using her thumb 320 to slide the actuator button 120. Engagement of the actuator button results in the dispensation of a sugar strip 200. Each dispensed strip protrudes through a slot disposed at the front of the casing. The protruding sugar strip is placed directly within the woman's oral cavity 310 without necessitating the use of her hands to grasp or manipulate the strip. This direct administration of sugar strips into the oral cavity reduces exposure to germs and liquids on a user's fingers that could contaminate the strip or damage its structural integrity.

The sugar strips of the present invention are sections of an oral of oral thin film. These thin films are constructed from sugar suspended in one or more hydrophobic polymers. Upon introduction to a liquid, the polymeric suspension medium decomposes, releasing sugar into the liquid and surrounding area. The interior of a human oral cavity is moistened by the regular generation of saliva, making oral tissues ideally suited for thin film placement. Locations along the upper tongue (lingual), tongue underside (sublingual), and cheek linings (bucchal) provide broad regions of moistened tissue perfect for enabling rapid dissolution of the thin film sugar strips. As the polymeric suspension medium dissolves the sugar released into the user's saliva is absorbed into the blood stream, thereby delivering a quick and clean sugar infusion. Creation of oral thin films is known in the art of drug delivery and the selection of appropriate polymeric suspension medium can be made by one of ordinary skill.

The type of sugar used in the sugar strips is not limited to one form. Dextrose, sucrose, and fructose sugars are suitable for use with thin film delivery and thus may be used with the present sugar strips. Use of dextrose is preferred, because of the ease of metabolization when compared with that of fructose. But, fructose in the form of fruit juice may be highly desirable to some users because of the natural flavoring it provides. Fructose and glucose blends such as that found in bee honey are also contemplated, due to their desirable flavor properties. In persons with severe diabetes, fructose infused sugar strips may be lease desirable because of the metabolization difficulties that the sugar can cause. Thus, it is desirable that several varieties of the sugar strip+dispenser system are available so that users can select the blood sugar management system best suited for their needs.

Figure 2:
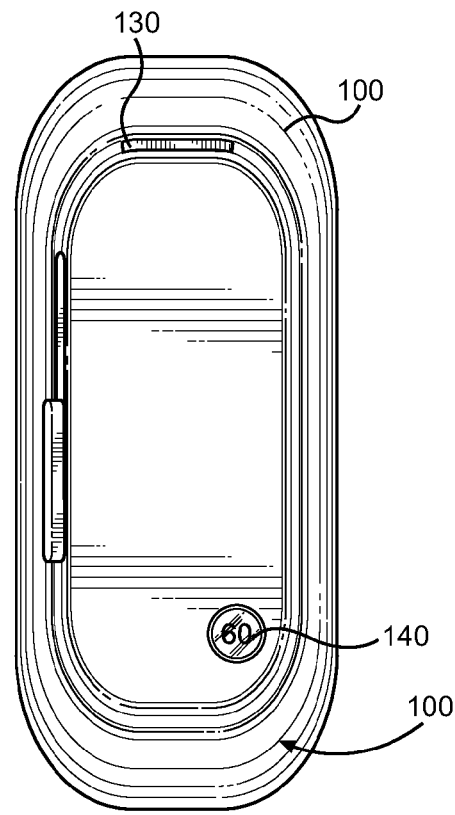
FIG. 2 shows an underside view of the dispenser of the blood sugar management system. The exit slot, counter, and actuating button are visible.

Turning to FIG. 2 there is shown an underside view of the sugar strip dispenser of the present system. The dispenser 100 has an exterior casing 110 with an exit slot 130 located at one end. When the actuator button 120 is depressed and slid along the length of the button track 121, a single sugar strip is moved forward through the slot until it protrudes therefrom. Every time a sugar strip is advanced, a counter displayed an updated indication of the number of sugar strips remaining within the dispenser. The current sugar strip count is viewable through a counter window 140 set into the dispenser casing. Translucent or transparent plastic is preferred for use as a counter window due to its durable and resilient properties. Connection between the casing and the counter window is sealed by adhesive or caulking material, thereby increasing the water resistance of the dispenser.

In the figure, the casing is shown having an upper and lower section that smoothly meets at a point between the upper and lower surface of the casing. This design creates an upper lip that extends over the lower section. Location of the exit slot along the lower section or the junction between the sections helps to prevent water and other moisture or contaminants from entering the exit slot while the device is in use. Keeping moisture and debris out of the casing is imperative in maintain structural integrity and sterility of the sugar strips. Further, the design reduces unnecessary surface area, making the dispenser easier to hold in a single hand. While this design is shown merely for exemplary purposes, and is not intended to limit the shape of the dispenser, it does show a manner of providing the desired beneficial properties.

Figure 3:
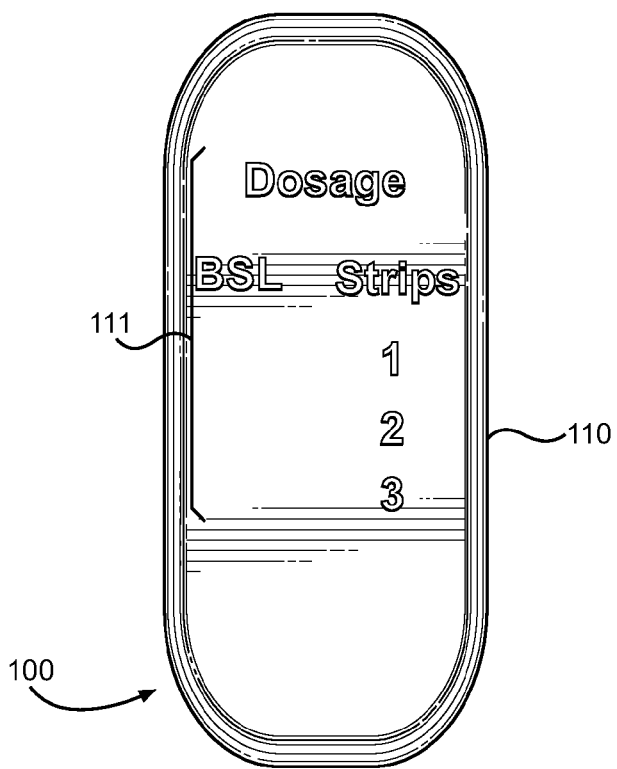
FIG. 3 shows an overhead view of the dispenser of the blood sugar management system. Indicia displaying dosage guidelines are printed along the upper surface of the dispenser.

The upper surface of the dispenser is shown in FIG. 3. The casing 110 of the dispenser 100 has dosage information 111 printed along the upper surface. Dosage information, such as the number of strips a person should intake given a certain blood sugar level, is highly dependent on each person's body chemistry and physical attributes. Height, weight, and other health concerns may affect the sugar intake needed by a particular person. Such information is provided by a doctor or pharmacist at the time the blood sugar management system is dispensed to a patient.

In the depicted example, a portion of a blood sugar concentration/sugar strip correlation chart is printed on the upper surface of the casing. Sugar strip dosages are pre printed in a column format, while the blood sugar concentration column remains blank. At the time a patient picks up their system, the pharmacist or doctor may print a label in column format that aligns blood sugar concentration numbers with the pre-printed sugar strip dosages when adhered to the casing. In this way, users have ready access to their dosage information and can quickly gauge the number of sugar strips they need to intake based on their current blood sugar levels. This feature assists users in reducing blood sugar fluctuations by facilitating metered sugar intake.

Figure 4:
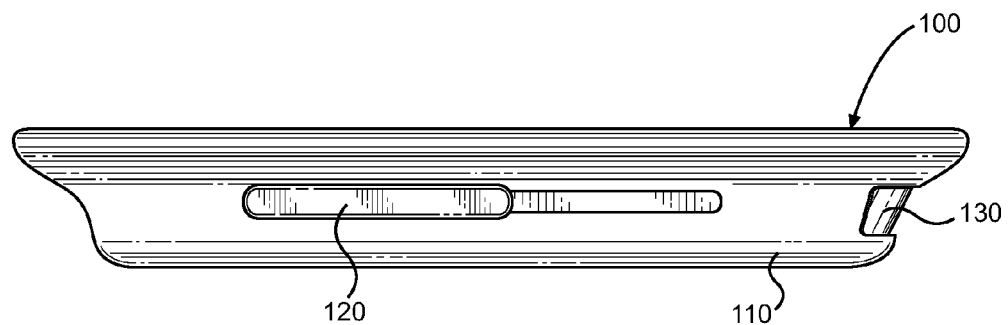
FIG. 4 shows a side view of the dispenser of the blood sugar management system. The actuator button is shown along with the exit slot.

The right side of the dispenser is shown in FIG. 4. An actuator button 120 is disposed along one side of the dispenser casing 110. The button slides along a button track 121, which is a channel extending along a portion of the side length. Here, the channel and button are shown along the lower section of the casing, but alternate configurations are acceptable. An exit slot is located near the front of the dispenser casing. The slit style opening provides an exit point for sugar strips advancing through the internal roll. A protective flap 410 abuts the interior surfaces of the casing surrounding the exit slot, and covers the slot when not in use. To reduce seepage of water and contaminants into the casing interior the protective flap should snuggly abut the area around the exit slot.

Figure 5:
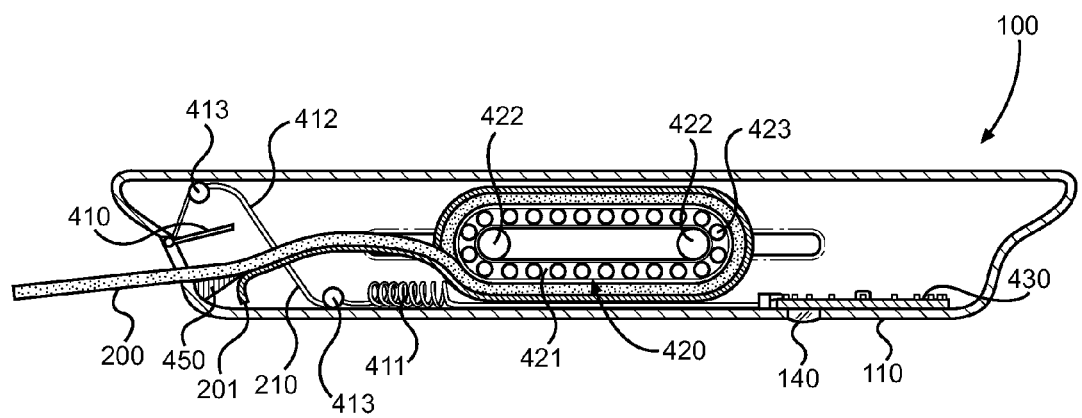
FIG. 5 shows a cross-section view of an exemplary embodiment of the sugar strip dispenser. The roll of sugar strips is shown with a strip extending out of the exit slot.

Referring now to FIG. 5, an exemplary implementation of the dispenser internal components are shown. The dispenser 100 has an outer casing 110 that may have uniform width or may have sections of varying width, as shown here. In the exemplary embodiment shown, the upper portion of the casing protrudes outward, creating a lip that overhands the lower portion.

A protective flap 410 assembly controls the position of the flap respective to the exit slot. A spring 411 is attached at one end to the interior of the actuator button, and at the other end to a wire 412. This wire is secured to the protective flap 410. When the actuator button is slide backward within its track, the spring and connected wire are pulled backward, resulting in the sliding back of the protective flap. To maintain the wire in position, placement pegs 413 are disposed along an interior wall. The wire is threaded over and under these pegs to create tension and prevent the wire from sliding around within the casing interior and interfering with the sugar strips. Peg ends are preferably flanged to keep the wire from sliding away from the pegs. Optionally, a track may be formed on either side of the exit slot (not shown) to guide the protective flap as it slides up and down during sugar strip dispensing.

The spring of the protective flap assembly serves the additional purpose of exerting force sufficient to return the actuator button to a resting position. When the button is slid backward along the button track, the spring is extended. Release of the button results in spring compression and return of the button to a neutral, resting position within the track.

Within the interior volume of the casing 110, a roll of sugar strips 200 is wound around a belt assembly 420. The roll of oral thin film sugar strips contains a predetermined number of strips having the same dimensions. A length of cellophane protective backing 201 is removably adhered to the underside of the strips. Inclusion of an insoluble backing provides a protective layer between adjacent strip layers on the roll, keeping strips from adhering to one another during storage. This backing is peeled away from the strips during the advancing process. A small separating edge 450 in the form of a wedge or blade is disposed near the lower edge of the exit slot. When a strip is advanced forward, the strip slides over the top of the separating edge and out the exit slot, but the protective backing is forced downward, into the bottom of the casing. Perforation may be used to designate where one strip begins and another ends. Further, perforating the strips will make it easier to remove a single strip from the roll. These features protect the sugar strip roll and facilitate easy dispensation of the strips without necessitating removal of the protective backing by a user.

The belt assembly 420 is shown in an exemplary embodiment in FIG. 5. A belt 421 is stretched between two or more support posts 422 in an ovular configuration. The roll of sugar strips is wound around the belt assembly. A plurality of engagement apertures 423 is disposed along the belt. When the actuator button (not shown) is depressed, a belt engagement post is inserted into one of the apertures. Sliding the button backward along its track forces the engagement post backwards, thereby advancing the belt and the sugar strips roll. Release of the button disengages the engagement post and allows the button to slide forward in its track to a resting position. In this way, sugar strips are dispensed by a user via depression and translation of the actuator button.

An exemplary counter dial 430 is shown in FIG. 5. The counter has a dial shape with numeric indicia disposed on the lower face. These indicia are visible through a window 140 in the bottom of the casing 110. Upon rotation of the counter dial, the visible indicium is changed. Each indicia is a numeric value associated with a number of sugar strips remaining in the roll 200, thus whenever the counter advances, the visible number decreases by one unit. Accurate tracking of sugar strip supply is essential for ensuring that users are aware of their on-hand sugar supply. Proper sugar supply preparedness enables users to go on outings and participate in activities without fear of dangerous low blood sugar episodes.

Figure 6:
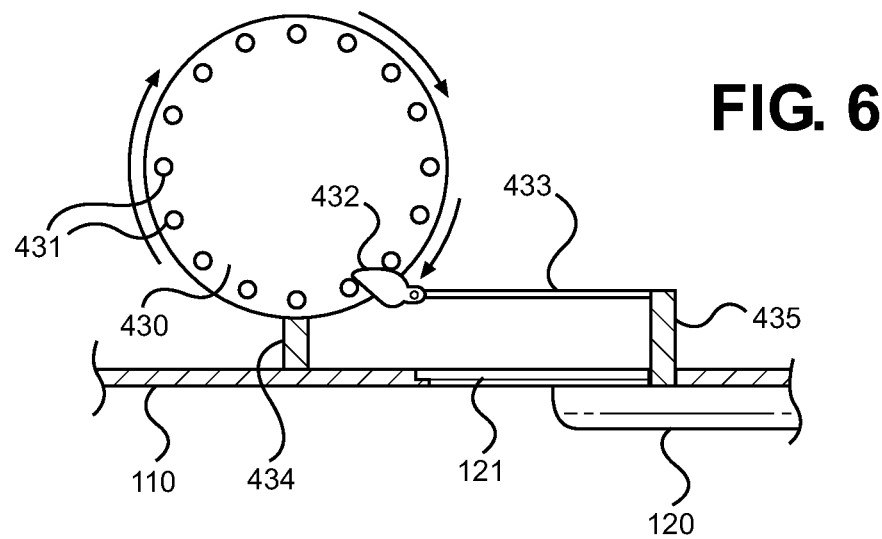
FIG. 6 shows a diagram of an exemplary advancing mechanism for the sugar strip counter.

A preferred embodiment of the counter dial is shown in FIG. 6. The counter dial 430 has a circular dial shape and lies near one wall of the dispenser casing 110. In the depicted example the counter dial lies on the same side of the dispenser as the actuator button 120 and the button track 121. A small extension arm connects a cam 432 and cam support arm 433 to the actuator button. The cam is pivotally/rotatably connected to the support arm to permit rotation about the connection point. On the upper surface of the counter dial is a plurality of evenly spaced dial pegs 431. The free end of the cam is placed between two of the pegs such that depression and sliding of the actuator button, forces the cam support arm and cam to move along the same axis as the button, which in turn exerts force on one of the dial pegs and turns the counter dial. It is preferred that the counter dial is positioned within a one way bracket, that does not permit backward rotation, thereby facilitating advancement of the counter but prohibiting slippage. A barrier wall 434 may also be provided to prevent the cam from extending too far forward and over-advancing the counter dial. Release of the actuator button exerts retrograde spring force on the cam and cam support arm, wherein the cam rotates, allowing it to slip from its current dial peg position back into a resting position.

Figure 7:
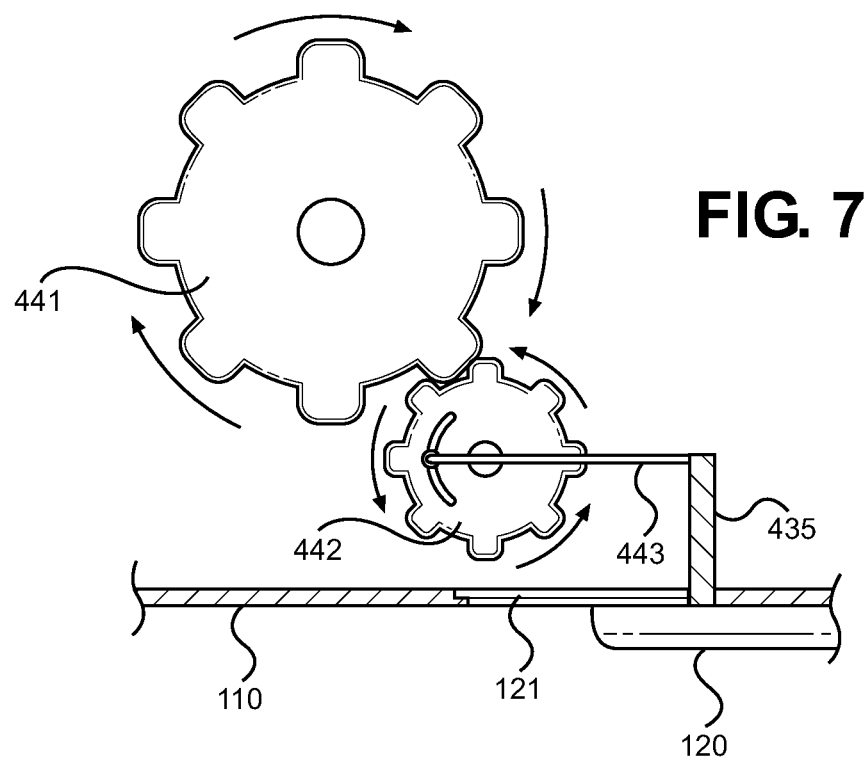
FIG. 7 shows a diagram of another exemplary advancing mechanism for the sugar strip counter.

An alternative exemplary embodiment of the counter dial is shown in FIG. 7. In this embodiment, the counter dial 430 is implemented using two or more gears. The actuator button 120 is connected to a gear support arm 443 via an extension arm 435. At an opposing end of the gear support arm, a small gear 442 is secured. The gear teeth 441 of the gear shaped counter dial engage with the teeth of the smaller dial. Thus, movement of the actuator button turns the small gear, which in turn rotates the counter dial. Modifications on the examples described herein will be apparent to one skilled in the art, and it should be noted that the exact configuration of the counter dial is not limited to these implementations.

Figure 8:
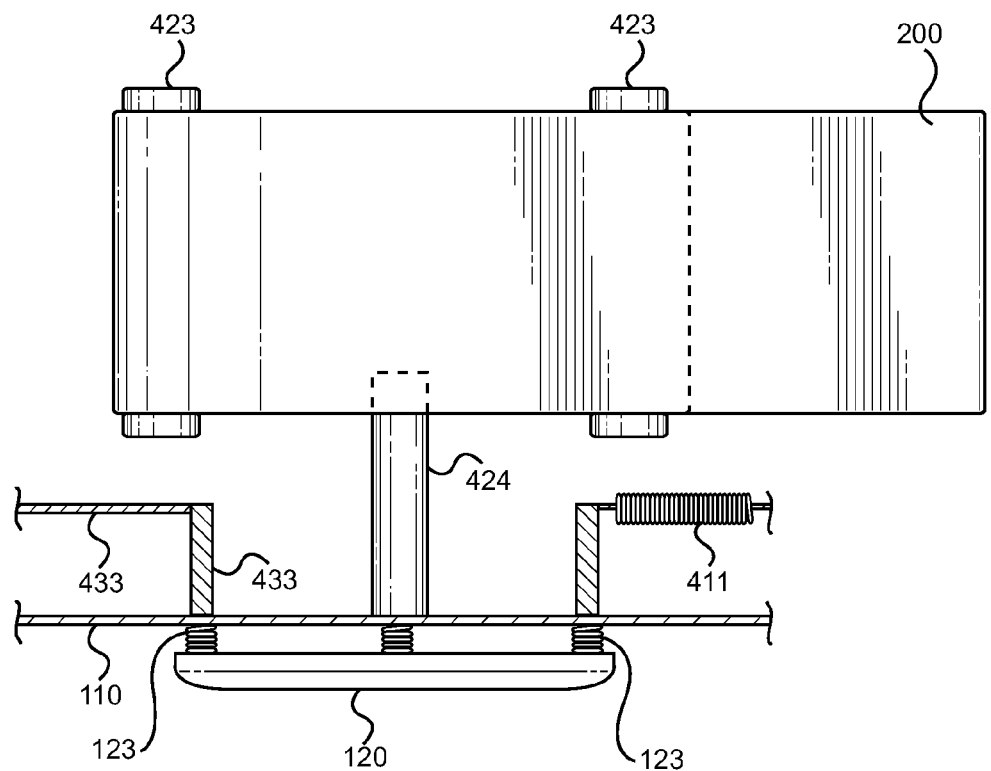
FIG. 8 shows a diagram of an exemplary embodiment of the actuator button of the sugar strip dispenser.

Referring now to FIG. 8, there is shown an overhead internal view of the actuator button in connection with the belt assembly. The actuator button 120 is attached to a number of springs 123 that enable depression of the button. The spring 141 of the protective flap assembly is secured to the forward button spring and the elongated arm 435 and cam support arm 433 are connected to the rear button spring. In between these structures, a belt engagement post 424 is connected to an intermediate button spring. When the actuator button is depressed, forced is exerted on the engagement post, pushing it into an engagement aperture (not shown) disposed on the side of the belt. Movement of the engagement post results in rotation of the belt around two or more support posts 423 and advances the roll of sugar strips 200.

Figure 9:
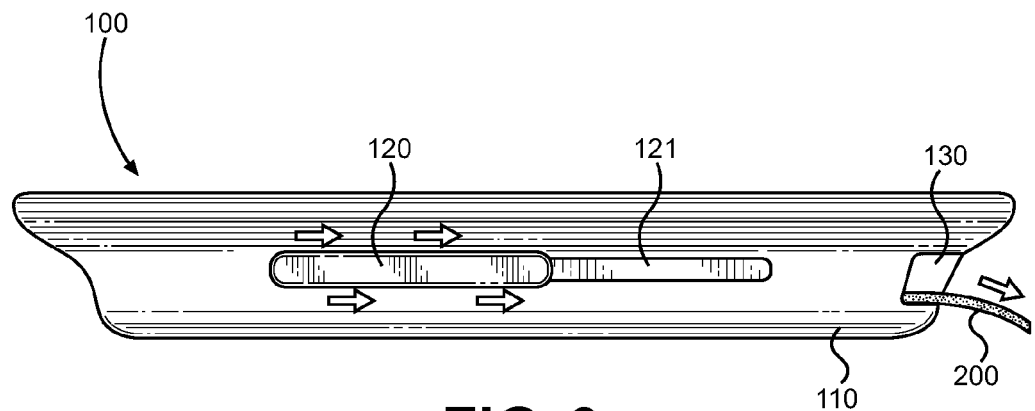
FIG. 9 shows a side view of the sugar strip dispenser of the blood sugar management system while in use.

Turning finally to FIG. 9, there is shown a side view of the sugar strip dispenser. The casing 110 of the dispenser 100 has an exit slot 130 disposed at one end. As shown in the drawing, the exit slot is open and in use. An actuator button 120 is moved backward along a button track 121 to affect dispensing of a single sugar strip 200. This depiction is the "in use" state of the system. When the button is released and returned to a natural, resting position within the button track, the protective flap will lower, sealing off the exit slot and cutting the sugar strip. For this reason, the bottom edge of the protective flap may be sharpened.

In use, a person needing regular intake of sugar checks the counter window on the dispenser to ensure that the number of remaining sugar strips is sufficient to meet their daily needs. Upon determining that the supply of sugar strips is sufficient, the user places the dispenser in an easy to reach location such as a pocket, purse, or jacket. If the user is diabetic, he or she may wish to check their blood sugar concentration levels with a self test kit throughout the day. In the event that a blood sugar test indicates a low BSC, or the user starts to experience symptoms of hypoglycemia, the dispenser should be immediately removed from its storage location. The user then consults the dosage information displayed on the upper surface of the dispenser to determine how many sugar strips should be taken. Next, the user holds the exit slot end of the dispenser near the opening to their mouth and then depresses and slides the actuator button along its track to dispense a sugar strip. Releasing the button drops the protective flap downward, severing the sugar strip from the roll. The sugar strip will fall onto the user's lips or tongue, where it begins to dissolve upon contract with moist oral tissues. This process is repeated as many times as needed to obtain the needed number of sugar strips.

The present invention is a blood sugar management system that provides users with a sanitary, discrete, and reliable way to intake sugar. Because the dispenser peels away protective covering and advances sugar strips into a "ready to ingest"

position, the user does not need to use his or her hands to place a strip in the mouth. This drastically reduces exposure to germs because the user's hands and fingers do not come into contact with the sugar strips.

Similarly, the system is discrete and easily concealable. The dispenser fits within the general area of a user's palm and requires only the use of a single thumb to advance a sugar strip into a useable position. By way of example, the user can grasp the dispenser in one hand, slide the button back, and discretely raise the dispenser to their mouth to place the dispensed sugar strip therein. This procedure is similar to the dispensation of a stick of gum. The system can thus be used during meetings, while at the movies, at public outings, and the like, without requiring the user to excuse themselves to a restroom.

A key feature of the system is that it reliably provides access to metered doses of sugar. For persons experiencing severe low blood sugar episodes, time is of the essence. Minutes and seconds can make the difference between mild symptoms and a lapse into a coma. It is imperative that persons with blood sugar imbalances gain immediate access to easily ingestible sugar. The present system addresses this need by providing single doses of a predetermined amount of sugar via an oral thin film delivery. To ensure that users do not run out of sugar strips when they are most needed, a supply counter is disposed on the strip dispenser. This counter updates, reducing the supply count, every time a sugar strip is dispensed. In this manner, the system helps users prepare for outings and daily activities by keeping all needed sugar supplies in a single compact package.

The overall shape and material construction of the dispenser may vary according to manufacturing needs. The configuration of internal components described herein is for exemplary purposes and are used to illustrate how the desired functions of the system can be mechanically achieved. Other mechanical configurations may be employed so long as the iterative counter, sugar strip roll, and protective flap are present and functional. Thus, the assemblies necessary for providing these functions can vary depending on the needs of users and manufacturers.

To this point, the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A portable blood sugar management system, comprising:
   a plurality of hydrophobic film sugar strips;
   a portable sugar strip dispenser comprising an exit slot and an internally disposed protective flap, which abuts and covers said exit slot when not in use, wherein said dispenser houses said sugar strips;
   an actuating mechanism operatively connected to said dispenser such that engagement of said actuator mechanism dispenses one of said sugar strips through said exit slot;
   a counter disposed on said dispenser and operatively connected to said actuating mechanism such that dispensation of one of said sugar strips via said actuating mechanism updates said counter to reflect a remaining supply of sugar strips within said dispenser.

2. The system of claim 1, wherein said plurality of sugar strips are connected in a roll.

3. The system of claim 1, wherein said sugar strips are constructed from an edible hydrophobic polymer and a sugar.

4. The system of claim 3, wherein said sugar is dextrose or sucrose.

5. The system of claim 1, wherein said actuating means is a button.

6. The system of claim 1, wherein said protective flap is operatively connected to said actuating mechanism, such that engagement of said actuating mechanism slides said protective flap away from said exit slot, exposing same.

7. The system of claim 1, wherein said sugar strips have a protective backing when stored.

8. The system of claim 7, wherein said protective backing is removed via a separating edge during dispensing of said sugar strips through said exit slot.

* * * * *